United States Patent
Goodnow, Jr. et al.

(10) Patent No.: US 6,784,298 B2
(45) Date of Patent: Aug. 31, 2004

(54) HYDANTOIN-CONTAINING GLUCOKINASE ACTIVATORS

(75) Inventors: Robert Alan Goodnow, Jr., Gillette, NJ (US); Kang Le, Clifton, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/454,041

(22) Filed: Jun. 4, 2003

(65) Prior Publication Data

US 2003/0225286 A1 Dec. 4, 2003

Related U.S. Application Data

(62) Division of application No. 09/843,466, filed on Apr. 26, 2001, now Pat. No. 6,583,288.
(60) Provisional application No. 60/201,498, filed on May 3, 2000.

(51) Int. Cl.$^7$ .................. C07D 417/14; C07D 401/14; A61K 31/427; A61K 31/4439; A61P 3/10
(52) U.S. Cl. .................. 548/195; 548/214; 548/315.1; 548/314.7; 548/315.4; 546/274.4; 546/15; 514/374; 514/389; 514/341
(58) Field of Search .................. 548/195, 214, 548/315.1, 314.7, 315.4; 546/274.4

(56) References Cited

U.S. PATENT DOCUMENTS

5,202,339 A * 4/1993 Mochida et al. ............. 514/327
6,320,050 B1 * 11/2001 Bizzarro et al. ............. 544/332
6,583,288 B2 * 6/2003 Goodnow et al. ....... 546/274.4

OTHER PUBLICATIONS

Liang Y, et al. Biochem. J. (1995) 309:167–173.
Neet, K. et al, Biochemistry (1990) 29:770–777.
Meglasson, M D. et al, Amer. J. Physiol. (1984) 246:E1–E13.
Glaser, B. et al, New England J. Med. (1998) 338:226–230.
Ferre, T. et al, FASEB J. (1996) 10:1213–1218.
Grupe, A. Cell (1995) 83:69–78.
Printz, R., Ann. Rev. Nutrition, (1993) 13:463–496.
Chipkin, S. et al, Joslin's Diabetes (1994) 97–115.
Colowick, S., The Enzymes (1973) 9:1–48.
Merrifield, R.B., Amer. Chem. Soc. (1963) 85:2149–2154.
Kaiser et al, Anal. Biochem. (1970) 34:595–598.

* cited by examiner

*Primary Examiner*—Evelyn Mei Huang
(74) *Attorney, Agent, or Firm*—George W. Johnston; Dennis P. Tramaloni; Eileen M. Ebel

(57) ABSTRACT

Hydantoin compounds which are active as glucokinase activators to increase insulin secretion which makes them useful for treating type II diabetes.

8 Claims, No Drawings

HYDANTOIN-CONTAINING GLUCOKINASE ACTIVATORS

CONTINUITY INFORMATION

This application is a divisional of U.S. Ser. No. 09/843,466, filed Apr. 26, 2001, now U.S. Pat. No. 6,583,288, which claims priority under 35 U.S.C. § 119(e) of provisional application Serial No. 60/201,498, filed May 3, 2000.

CROSS-REFERENCE TO RELATED APPLICATIONS

This application is related to U.S. Ser. No. 09/526,143 filed Mar. 15, 2000 and U.S. Ser. No. 09/532,506 filed Mar. 21, 2000.

BACKGROUND OF THE INVENTION

Glucokinase (GK) is one of four hexokinases found in mammals [Colowick, S. P., in *The Enzymes*, Vol. 9 (P. Boyer, ed.) Academic Press, New York, N.Y., pages 1–48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in *Joslin's Diabetes* (C. R. Khan and G. C. Wier, eds.), Lea and Febiger, Philadelphia, Pa., pages 97–115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial ($\approx$10–15 mM) levels following a carbohydrate-containing meal [Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463–496, 1993]. These findings contributed over a decade ago to the hypothesis that GK functions as a glucose sensor in β-cells and hepatocytes (Meglasson, M. D. and Matschinsky, F. M. *Amer. J. Physiol.* 246, E1–E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69–78, 1995; Ferrie, T., Riu, E., Bosch, F. et al., *FASEB J.*, 10, 1213–1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167–173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226–230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

SUMMARY OF THE INVENTION

This invention provides a compound, comprising a substituted hydantoin of the formula:

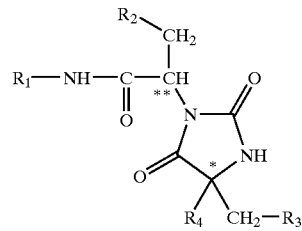

wherein
$R_1$ is a five- or six-membered aromatic heterocyclic ring having one to three heteroatoms selected from nitrogen, oxygen, and sulfur, which ring is unsubstituted or substituted with halo, amino, hydroxylamino, nitro, cyano, sulfonamido, lower alkyl, perfluoro lower alkyl, lower alkyl thio, perfluoro-lower alkyl thio, lower alkyl sulfonyl, perfluoro-lower alkyl sulfonyl, lower alkyl sulfinyl, or $—(R_5)_n—C(O)—OR_6$;
$R_2$ is a cycloalkyl ring containing from 5 to 7 carbon atoms;
$R_3$ is hydrogen, lower alkyl, a cycloalkyl ring containing from 5 to 7 carbon atoms, unsubstituted aryl, aryl substituted with halo or hydroxy, or an unsubstituted five- or six-membered aromatic heterocyclic ring having one or two heteroatoms selected from nitrogen, oxygen, and sulfur;
$R_4$ is hydrogen, lower alkyl, or $R_3$ and $R_4$ together with the carbon atom to which they are attached form a cycloalkyl ring containing 5 to 7 carbon atoms;
$R_5$ is —C(O)— or lower alkyl;
$R_6$ is lower alkyl;
n is 0 or 1; * and ** each designate an asymmetric centers, and pharmaceutically acceptable salts thereof.

The compounds of Formula I have been found to activate glucokinase. Glucokinase activators are useful for increasing insulin secretion in the treatment of type II diabetes. Therefore compounds of this invention are useful to increase insulin secretion in view of their activity as glucokinase activators.

DETAILED DESCRIPTION OF THE INVENTION

This invention is directed to compounds of Formula I above. The invention is particularly directed to compounds as follows, where:

$R_2$ and $R_3$ are both cyclohexyl, or
$R_3$, when it is lower alkyl, is methyl, ethyl, propyl, or butyl, or
$R_4$, when it is lower alkyl, is methyl or ethyl (especially compounds where $R_3$ and $R_4$ are both so defined), or R₁, when substituted, is substituted with halo, lower alkyl, or
—(R₅)ₙ—C(O)—OR₆,
or compounds where any two or more, or all, of these conditions are met. For any compound of this invention where R₁, R₂, or R₃ are not specified, it is preferred that the variable is as described in this paragraph.

Certain preferred compounds of Formula I include a compound where R₁ is substituted or unsubstituted thiazolyl (Compound A). Among the embodiments of Compound A are those compounds where R₁ is thiazolyl substituted with halo, lower alkyl, or —(R₅)ₙ—C(O)—OR₆, and especially with —(R₅)ₙ—C(O)—OR₆. (Compound A-1). In Compound A-1, it is preferred that R₂ is cyclopentyl or cyclohexyl. It is also preferred that R₃ is cyclopentyl or cyclohexyl. It is preferred that R₄ is hydrogen. It is especially preferred that R₂ and R₃ are cyclohexyl.

In preferred embodiments of Compound A-1, R₂ and R₃ are cyclopentyl or cyclohexyl, and R₄ is hydrogen (Compound A-1a). In one embodiment of Compound A-1a, n is 0 (e.g., the thiazolyl is substituted with —C(O)—OR₆). Examples of such compounds are (S,S)-2-[[3-cyclohexyl-2-[4-(cyclohexyl)methyl-2,5-dioxoimidazolidin-1-yl]propanoyl]amino]thiazole-4-carboxylic acid methyl ester.

(S,S)-2-[[2-[4-(cyclohexyl)methyl-2,5-dioxoimidazolidin-1-yl]-3-cyclopentylpropanoyl]amino]thiazole-4-carboxylic acid methyl ester.

(S,S)-2-[[3-cyclopentyl-2-[4-(cyclopentyl)methyl-2,5-dioxoimidazolidin-1-yl]propanoyl]amino]thiazole-4-carboxylic acid methyl ester.

(S,S)-2-[[3-cyclohexyl-2-[4-(cyclopentyl)methyl-2,5-dioxoimidazolidin-1-yl]propanoyl]amino]thiazole-4-carboxylic acid methyl ester.

In such a compound, R₂ and R₃ may both be cyclohexyl, for example (S,S)-2-[[3-cyclohexyl-2-[4-(cyclohexyl)methyl-2,5-dioxoimidazolidin-1-yl]propanoyl]amino]thiazole-4-carboxylic acid methyl ester.

In another embodiment of Compound A-1a, R₅ is —C(O)— or lower alkyl (e.g., the thiazolyl is substituted with —C(O)—C(O)—OR₆ or -lower alkyl-C(O)—OR₆). In addition, in such compounds R₂ and R₃ may be cyclohexyl. Examples of such compounds are (S,S)-[2-[[3-cyclohexyl-2-[4-(cyclohexyl)methyl-2,5-dioxoimidazolidin-1-yl]propanoyl]amino]thiazole-4-yl]oxoacetic acid ethyl ester and (S,S)-[2-[[3-cyclohexyl-2-[4-(cyclohexyl)methyl-2,5-dioxoimidazolidin-1-yl]propanoyl]amino]thiazole-4-yl]acetic acid ethyl ester.

In another embodiment of Compound A1, R₂ is cyclopentyl or cyclohexyl (Compound A-1b). In one embodiment of Compound A-1b, R₃ is substituted or unsubstituted phenyl and R₄ is hydrogen. Examples of these compounds are (S,S)-2-[[2-(4-benzyl-2,5-dioxoimidazolidin-1-yl)-3-cyclohexylpropanoyl]amino]thiazole-4-carboxylic acid methyl ester.

2-[[(S)-2-[(R)-4-(4-chlorobenzyl)-2,5-dioxoimidazolidin-1-yl]-3-cyclohexylpropanoyl]amino]thiazole-4-carboxylic acid methyl ester.

(S,S)-2-[[3-cyclohexyl-2-[2,5-dioxo-4-(4-hydroxybenzyl)imidazolidin-1-yl]propanoyl]amino]thiazole-4-carboxylic acid methyl ester.

(S,S)-2-[[3-cyclohexyl-2-[2,5-dioxo-4-(3-hydroxybenzyl)imidazolidin-1-yl]propanoyl]amino]thiazole-4-carboxylic acid methyl ester, and 2-[[(S)-3-cyclohexyl-2-[(R,S)-2,5-dioxo-4-(4-fluorobenzyl)imidazolidin-1-yl]propanoyl]amino]thiazole-4-carboxylic acid methyl ester.

In another embodiment of Compound A-1b, at least one of R₃ and R₄ are lower alkyl. Examples of such compounds are (S)-2-[[3-cyclohexyl-2-(4,4-dimethyl-2,5-dioxoimidazolidin-1-yl)propanoyl]amino]thiazole-4-carboxylic acid methyl ester, and 2-[[(S)-3-cyclohexyl-2-[(R)-2,5-dioxo-4-propylimidazolidin-1-yl]propanoyl]amino]thiazole-4-carboxylic acid methyl ester.

In yet another embodiment of Compound A-1b, R₃ is naphthyl and R₄ is hydrogen. An example of such a compound is (S,S)-2-||3-cyclohexyl-2-[2,5-dioxo-4-(naphthalen-2-yl)methylimidazolidin-1-yl]propanoyl]thiazole-4-carboxylic acid methyl ester.

In another embodiment of Compound A-1b, R₃ and R₄ together with the carbon atoms to which they are attached form a cycloalkyl ring containing 5 to 7 carbon atoms. An example of such a compound is (S)-2-[[3-cyclohexyl-2-(2,4-dioxo-1,3-diazaspiro[4.4]non-3-yl)propanoyl]amino]thiazole-4-carboxylic acid methyl ester.

And in another embodiment of Compound A-1b, R₃ is an unsubstituted five- or six-membered aromatic heterocyclic ring having one or two heteroatoms selected from nitrogen, oxygen, and sulfur. An example of such a compound is (S,S)-2-[[3-cyclohexyl-2-[2,5-dioxo-4-(thiophen-2-yl)methylimidazolidin-1-yl]propanoyl]amino]thiazole-4-carboxylic acid methyl ester.

In one embodiment of Compound A (a compound of Formula I wherein R₁ is substituted or unsubstituted thiazolyl), R₁ is unsubstituted thiazolyl (Compound A-2). It is preferred that R₂ and R₃ are cyclohexyl and R₄ is hydrogen. An example of such a Compound A-2 is (S,S)-3-cyclohexyl-2-[4-(cyclohexyl)methyl-2,5-dioxoimidazolidin-1-yl]-N-(thiazole-2-yl)propanamide.

In other preferred compounds of Formula I, R₁ is substituted or unsubstituted pyridine (Compound B). It is preferred that R₂ is cyclopentyl or cyclohexyl, especially cyclohexyl. It is also preferred that R₃ is cyclopentyl or cyclohexyl, especially cyclohexyl. It is preferred that R₄ is hydrogen.

In one embodiment of Compound B, R₂ is cyclohexyl. In such a compound where R₂ is cyclohexyl, it is preferred that R₃ is cyclohexyl and R₄ is hydrogen (Compound B-1).

In one embodiment of Compound B-1, R₁ is substituted pyridine. Preferably the pyridine is substituted with —(R₅)ₙ—C(O)—OR₆, especially where n is 0 and R₆ is lower alkyl, such as methyl (e.g., methoxycarbonyl). Examples of such compounds are (S,S)-3-cyclohexyl-2-[4-(cyclohexyl)methyl-2,5-dioxoimidazolidin-1-yl]-N-(5-methylpyridin-2-yl)propanamide.

(S,S)-6-[[3-cyclohexyl-2-[4-(cyclohexyl)methyl-2,5-dioxoimidazolidin-1-yl]propanoyl]amino]nicotinic acid methyl ester, and (S,S)-N-(5-chloropyridin-2-yl)-3-cyclohexyl-2-[4-(cyclohexyl)methyl-2,5-dioxoimidazolidin-1-yl]propanamide.

In another embodiment of Compound B-1, $R_1$ is unsubstituted pyridine. An example of such a compound is (S,S)-3-cyclohexyl-2-[4-(cyclohexyl)methyl-2,5-dioxoimidazolidin-1-yl]-N-(pyridin-2-yl)propanamide.

In the compound of Formula I the "*" and "" illustrate the two separate asymmetric centers. The (S) enantiomer at the position designated by "" is preferred. However the compounds of this invention may be pure (R)(R), pure (S)(S), pure (R)(S), pure (S)(R) or any mixture of pure enantiomers.

As used throughout this application unless otherwise specified, the term "lower alkyl" includes both straight chain and branched chain alkyl groups having from 1 to 6 or 1 to 7 carbon atoms, such as methyl, ethyl, propyl, isopropyl, preferably methyl and ethyl. Unless otherwise specified, propyl is taken to include both forms of propyl (e.g., isopropyl, n-propyl) and butyl is taken to include all forms of butyl (e.g., isobutyl, n-butyl, tert-butyl). Preferred at $R_3$ is methyl, ethyl, propyl, or butyl. Preferred at $R_4$ is methyl or ethyl.

The term "cycloalkyl ring" may be a ring of from three to seven carbon atoms, but preferably from five to seven carbon atoms, especially cyclopentyl, cyclohexyl, cyclobutyl and cyclopropyl. The more preferable cycloalkyl groups contain from 5 to 6 carbon atoms, e.g., cyclopentyl and cyclohexyl, and cyclohexyl is most preferable. As used herein, "perfluoro-lower alkyl" means any lower alkyl group wherein all of the hydrogens of the lower alkyl group are substituted or replaced by fluoro. Among the preferred perfluoro-lower alkyl groups are trifluoromethyl, pentafluoroethyl, heptafluoropropyl, etc.

As used herein, "lower alkyl thio" means a lower alkyl group as defined above where a thio group is bound to the rest of the molecule. Similarly "perfluoro-lower alkyl" thio means a perfluoro-lower alkyl group as defined above where a thio group is bound to the rest of the molecule. As used herein, "lower alkyl sulfonyl" or "lower alkyl sulfinyl" means a lower alkyl group as defined above where a sulfonyl or sulfinyl group is bound to the rest of the molecule. Similarly "perfluoro-lower alkyl sulfonyl" means a perfluoro-lower alkyl group as defined above where a sulfonyl group is bound to the rest of the molecule.

When $R_3$ and $R_4$ together with the carbon atom to which they are attached form a cycloalkyl ring containing five to seven carbon atoms, this includes the ring carbon atom and the methylene linking the ring carbon atom and $R_4$ such that if $R_3$ and $R_4$ are each methylene, cyclobutyl is formed. If $R_3$ is methylene and $R_4$ is ethylene, cyclopentyl is formed, etc.

As used herein, the terms "halogen" or "halo" unless otherwise specified, designates all four halogens, i.e. fluorine, chlorine, bromine and iodine.

$R_1$ is, and $R_3$ can be any five- or six-membered aromatic heterocyclic ring containing from one to three, preferably from one to two, heteroatoms selected from the group consisting of sulfur, oxygen or nitrogen. Any such five- or six-membered aromatic heterocyclic ring can be used in accordance with this invention. Among the preferred rings for $R_1$ are thiazole and pyridine (especially pyridine), and a preferred ring for $R_3$ is thiophene. $R_1$, and $R_3$ when $R_3$ is a heterocyclic ring, is connected to the remainder of the molecule of Formula I through a ring carbon atom. When $R_1$ is substituted as described in Formula I, the substituent is on a ring carbon atom. $R_1$ is preferably monosubstituted, but may be di or tri substituted. A preferred substituent, especially for pyridine, is lower alkoxy (preferably methoxy) carbonyl.

As used herein the term "aryl" signifies an aromatic hydrocarbon ring having six or ten carbon atoms such as phenyl or naphthyl.

The compounds of this invention may be produced by the reaction schemes provided below.

The term "resin" designates any conventional polymer resin which has suitable characteristics for use in solid phase peptide synthesis. A resin with the suitable characteristics is inert, physically stable, insoluble in inorganic solvents, and has a linker functionality which is labile under known chemical conditions. Preferred are polystyrene resins having chemically labile functional linkers such as trityl resins and especially Wang resins.

The term "amino protecting group" designates any conventional amino protecting group which can be cleaved to yield the free amino group. The preferred protecting groups are the conventional amino protecting groups utilized in peptide synthesis. Especially preferred are those amino protecting groups which are cleavable under treatment with secondary dialkyl amines. A particularly preferred amino protecting group is 9H-fluoren-9-ylmethoxy carbamate.

"Orthogonal" is the term used to describe the relationship of the amino protecting group to the resin. The resin and the amino protecting group must be compatible, in that the resin-peptide bond and the amino protecting group should not labile under the same conditions. During synthesis of a given compound, one should be able to cleave the amino protecting groups off the compound while leaving the compound attached to the resin. In other words, the conditions under which the amino protecting group comes off the compound should not also cause the compound to come off the resin. It is preferred that the amino protecting group be cleavable under basic or weakly acidic conditions, because the preferred Wang-type resins are cleavable under strongly acidic conditions (i.e. about pH 0 to about pH 1) A skilled person will readily be able to determine the necessary conditions to select an orthogonal amino protecting group—resin set.

The term "pharmaceutically acceptable salts" as used herein include any salt with both inorganic or organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, paratoluene sulfonic acid and the like. The term "pharmaceutically acceptable salts" also includes any pharmaceutically acceptable base salt such as amine salts, trialkyl amine salts and the like. Such salts can be formed quite readily by those skilled in the art using standard techniques.

In accordance with this invention, the compounds of Formula I are produced by the following reaction schemes. Any compound of Formula I may be produced as shown in Reaction Scheme 1. The compounds of Formula I-A are produced as shown in Reaction Scheme 2. Reaction Scheme 3 shows how to produce N-Fmoc-aminothiazole-4-carboxylic acid, which is compound 3 of Scheme 2 where PG is the protecting group Fmoc.

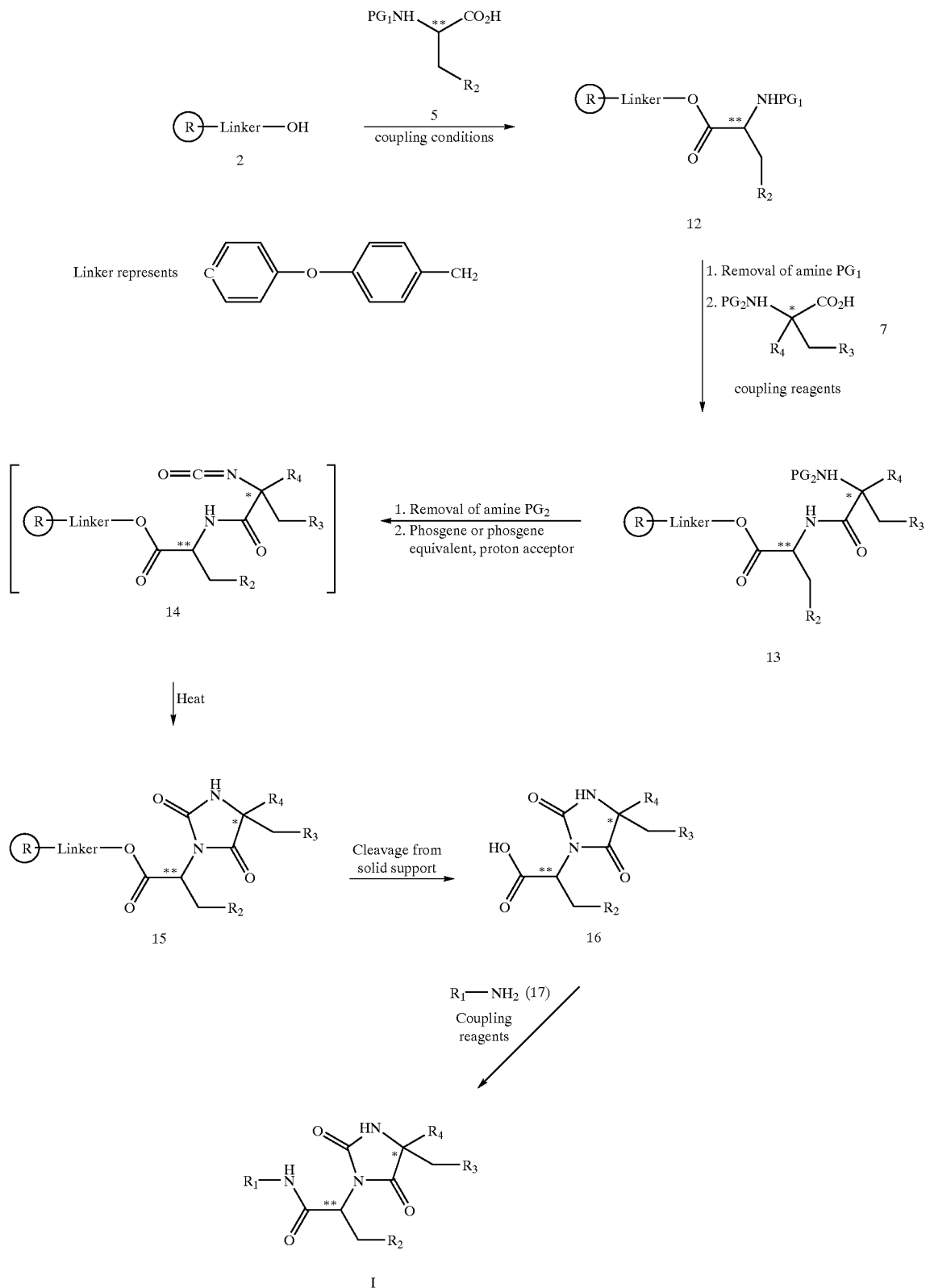
Reaction Scheme 1
wherein $R_1$, $R_2$, $R_3$ and $R_4$ are as previously described and $PG_1$ and $PG_2$ are amine protecting groups which may or may not be equivalent, that are removable under conditions compatible with the Linker-O bond.

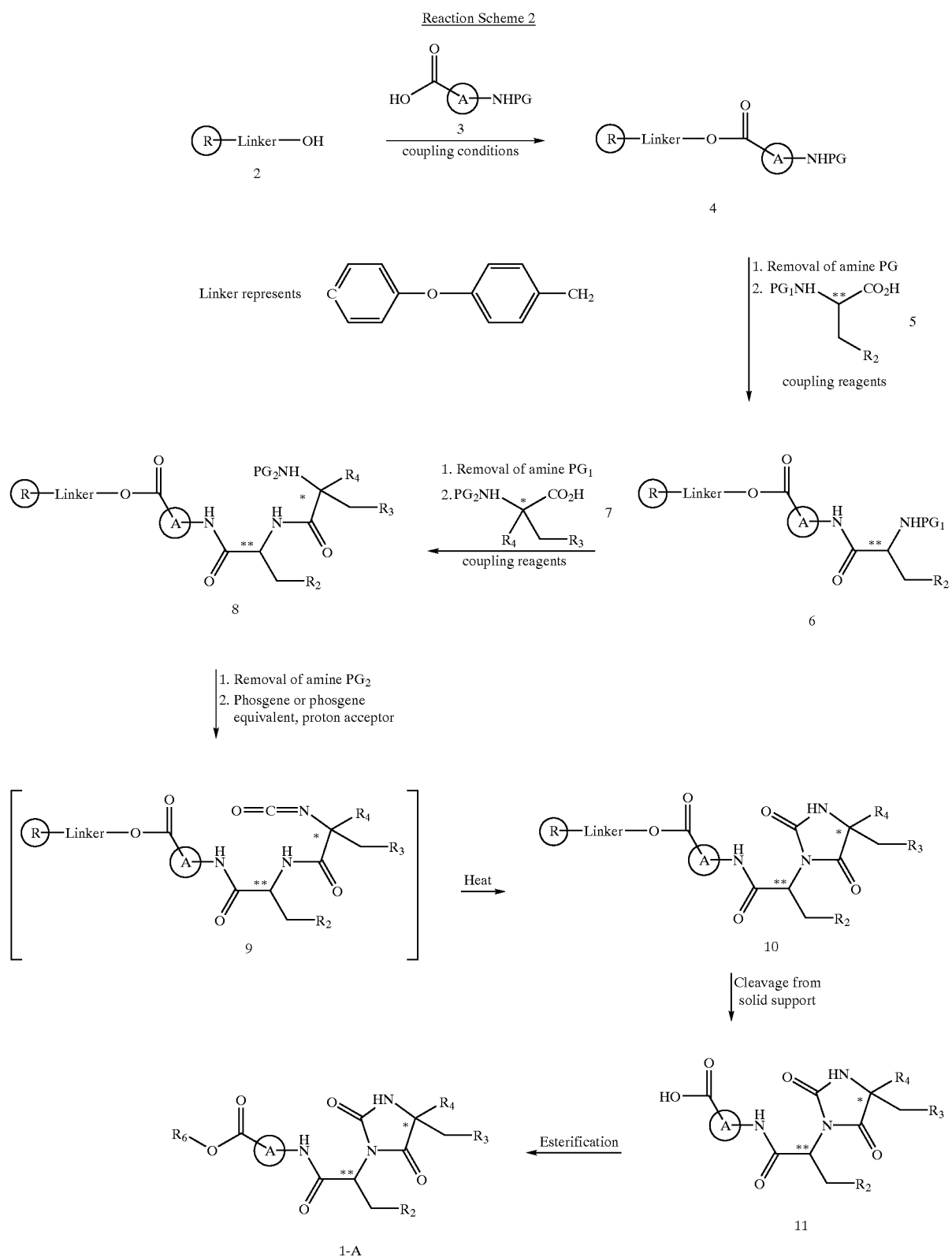

Reaction Scheme 2 wherein $R_2$, $R_3$, $R_4$ and $R_6$ are as previously described and PG, $PG_1$ and $PG_2$ are amine protecting groups which may or may not be equivalent, that are removable under conditions compatible with the linker-O bond and where the ring A represents a five or six membered heteroaromatic ring having one, two or three hetero atoms selected from nitrogen, oxygen or sulfur.

Reaction Scheme 3

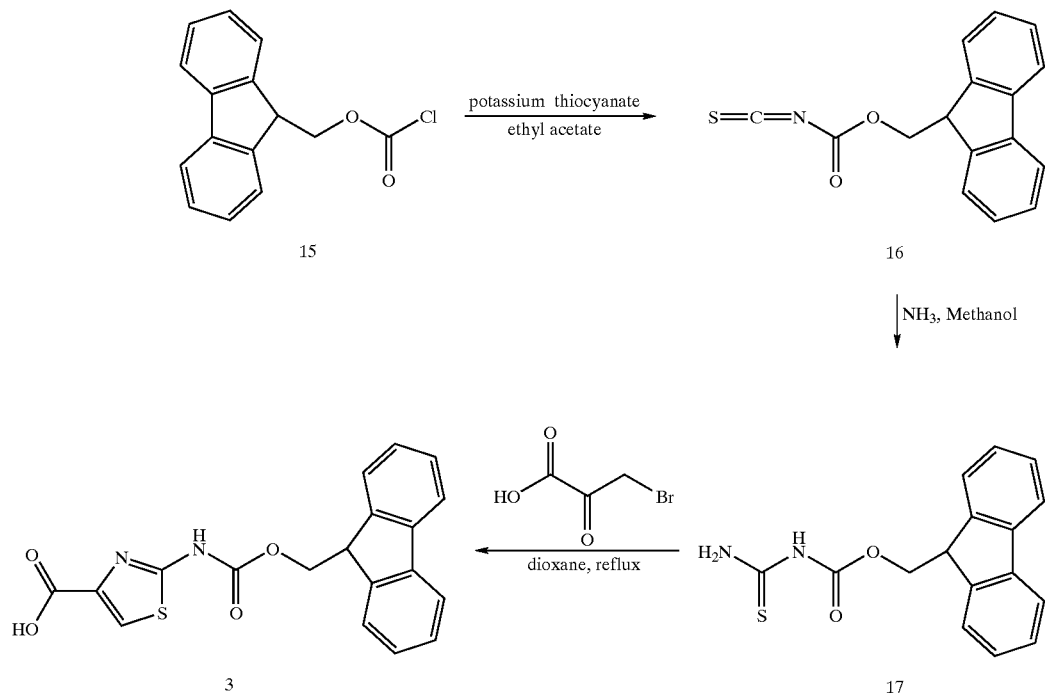

The synthesis of the compounds of this invention may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the compound.

Such conventional procedures for synthesizing the novel compounds of the present invention include for example any solid phase peptide synthesis method. In such a method the synthesis of the novel compounds can be carried out by sequentially incorporating the desired amino acid residues one at a time into the growing peptide chain according to the general principles of solid phase methods [Merrifield, R. B., J. Amer. Chem. Soc. 1963, 85, 2149–2154; Barany et al., The Peptides, Analysis, Synthesis and Biology, Vol. 2, Gross, E. and Meienhofer, J., Eds. Academic Press 1–284 (1980); Bunin, B., Combinatorial Index, Academic Press (1998)].

Common to chemical syntheses of peptides is the protection of reactive side chain groups of the various amino acid moieties with suitable protecting groups, which will prevent a chemical reaction from occurring at that site until the protecting group is ultimately removed. Usually also common is the protection of the alpha amino group of an amino acid or fragment while that entity reacts at the carboxyl group, followed by the selective removal of the alpha amino protecting group and allow a subsequent reaction to take place at that site. While specific protecting groups are mentioned below in regard to the solid phase synthesis method, it should be noted that each amino acid can be protected by any protective group conventionally used for the respective amino acid in solution phase synthesis.

For example, alpha amino groups may be protected by a suitable protecting group selected from aromatic urethane-type protecting groups, such as benzyloxycarbonyl (Z) and substituted benzyloxycarbonyl, such as p-chloro-benzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz); aliphatic urethane-type protecting groups, such as t-butyloxycarbonyl (Boc), diisopropylmethoxycarbonyl, isopropoxycarbonyl, and allyloxycarbonyl. In the present case, Fmoc is the most preferred for alpha amino protection. Guanidino groups may be protected by a suitable protecting group selected from nitro, p-toluenesulfonyl (Tos), Z, pentamethylchromanesulfonyl (Pmc), adamantyloxycarbonyl, and Boc. Pmc is the most preferred for arginine (Arg).

The solvents dichloromethane, dimethylformamide (DMF) and N-methylpyrrolidinone and toluene may be purchased from Fisher or Burdick and Jackson and may be used without additional distillation. Trifluoroacetic acid was purchased from Halocarbon or Fluka and used without further purification. Diisopropylcarbodiimide and diisopropylethylamine (DIPEA) was purchased from Fluka or Aldrich and used without further purification. 1-Hydroxybenzotriazole (HOBT) may be purchased from Sigma Chemical Co. and used without further purification. Protected amino acids, unless otherwise specified, are generally preferably of the L configuration and may be obtained commercially from Bachem, Advanced ChemTech, or Neosystem. Such amino acids may also be chemically synthesized using any one of several well known methods of amino acid synthesis. The configuration of the amino acids 5 and 7 used to prepare a given compound of this invention will determine the configuration of the ** and * positions respectively of Formula I. Therefore, it is useful to select the amino acid configuration with the desired final configuration in mind. L amino acids have the (S) absolute configuration and D amino acids have the (R) absolute configuration.

Compounds of this invention may be prepared using solid phase synthesis following the principles and general methods described by Merrifield or by Bunin, although other equivalent chemical synthesis known in the art could be used as previously mentioned. Solid phase synthesis is commenced from the C-terminal end of the peptide by coupling a N-protected amino acid to a suitable resin. Such a starting material can be prepared by attaching an N-protected amino acid by an ester linkage to a p-benzyloxybenzyl alcohol (Wang) resin, or by an amide bond between an Fmoc-Linker, such as p-[(R,S)-α-[1-(9H-fluoren-9-yl)-methoxyformamido]-2,4-dimethyloxybenzyl]-phenoxyacetic acid (Rink linker) to a benzhydrylamine (BHA) resin. Preparation of the hydroxymethyl resin is well known in the art. Wang resin supports are commercially available and generally used when the desired peptide being synthesized has an ester or a substituted amide at the C-terminus. To form the starting resin bound amino acid, a Fmoc N-protected amino acid is activated by the formation of a mixed anhydride which in turn couples with the hydroxymethyl resin though an ester bond. Several reagents are used to form mixed anhydrides in which the carbonyl group originating from the C-terminal amino acid is preferentially activated to nucleophilic attack by the hydroxymethyl residues in the Wang resin, through either electronic or steric effects. For example, appropriate compounds used in the formation of the mixed anhydrides are trimethylacetyl chloride, 2,6-dichlorobenzoyl chloride and 2,4,6-trichlorobenzoyl chloride, preferably 2,6-dichlorobenzoyl chloride.

Subsequently, the amino acids or mimetics are then coupled onto the Wang resin using the Fmoc protected form of the amino acid or mimetic, with 2–5 equivalents of amino acid and a suitable coupling reagent. After each coupling, the resin may be washed and dried under vacuum. Loading of the amino acid onto the resin may be determined by amino acid analysis of an aliquot of Fmoc-amino acid resin or by determination of Fmoc groups by UV analysis.

The resins are carried through one or two cycles to add amino acids sequentially. In each cycle, the N-terminal Fmoc protecting group is removed under basic conditions from the resin bound amino acid. A secondary amine base such as piperidine, piperazine or morpholine, preferably piperidine (20–40% v/v) in an inert solvent, for example, N,N-dimethylformamide is particularly useful for this purpose. Following the removal of the alpha amino protecting group, the subsequent protected amino acids are coupled stepwise in the desired order to obtain an N-Fmoc protected peptide-resin. The activating reagents used for coupling of the amino acids in the solid phase synthesis of the peptides are well known in the art. For example, appropriate coupling reagents for such syntheses are [(benzotriazol-1-yl)oxy]tris(dimethylamino) phosphonium hexafluorophosphate (BOP), [(benzotriazol-1-yl)oxy]tris(pyrrolidino)-phosphonium hexafluorophosphate (PyBOP), O-(1H-benzotriazole-1-yl)-N,N,N',N'-tetramethyluronium hexafluorophosphate (HBTU), and diisopropylcarbodiimide (DIC), preferably HBTU and DIC. Other activating agents as described by Barany and Merrifield [The Peptides, Vol. 2, J. Meienhofer, ed., Academic Press, 1979, pp 1–284] may be utilized. The couplings are conveniently carried out in an inert solvent, such as N,N-dimethylformamide or N-methylpyrrolidinone, preferably N-methylpyrrolidinone, optionally in the presence of a substance that minimizes racemization and increases the rate of reaction. Among such substances are 1-hydroxybenzotriazole (HOBT), 3,4-dihydro-3-hydroxy-4-oxo-1,2,3-benzotriazine (HOOBT), 1-hydroxy-7-azabenzotriazole (HOAT), and N-hydroxysuccinimide (IIOSu). In the present instance, HOBT is preferred.

The protocol for a typical coupling cycle is as follows (Method B):

| Step | Reagent | Time |
| --- | --- | --- |
| 1 | 20% piperidine/DMF | 30 min |
| 2 | DMF | 3 × 30 sec |
| 3 | methanol | 3 × 30 sec |
| 4 | dichloromethane | 3 × 30 sec |
| 5 | coupling | overnight |
| 6 | DMF | 3 × 30 sec |
| 7 | methanol | 3 × 30 sec |
| 8 | dichloromethane | 3 × 30 sec |

Solvents for all washings and couplings may be measured to volumes of, for example, 10–20 ml/g resins. Coupling reactions throughout the synthesis may be monitored by assays, such as the Kaiser ninhydrin test, to determine extent of completion [Kaiser et at. Anal. Biochem. 1970, 34, 595–598].

When the requisite number of amino acid units have been assembled on the resin, the N-terminal Fmoc group may be cleaved using Steps 1–4 of Method B and the deprotected amine is reacted with phosgene or a phosgene equivalent to form an isocyanate. The reagent of choice in this transformation is trichloromethyl chloroformate (diphosgene). The reaction is carried out in an inert solvent, for example dichloromethane, in the presence of a proton acceptor. When a suspension of the resin bound isocyanate is heated, cyclization occurs wherein the isocyanate moiety condenses with the nitrogen of the neighboring amide group to form a 2,5-dioxoimidazolidine ring.

The compounds may be cleaved from the resin by the following procedure, conditions which also remove other protecting groups if they are present. The peptide-resins are shaken in a mixture (1:1) of trifluoroacetic acid in dichloromethane, optionally in the presence of a cation scavanger, for example ethanedithiol, dimethylsulfide, anisole or triethylsilane, at room temperature for 60 min. The cleavage solution may be filtered free from the resin, concentrated to dryness, and the product then used per se in subsequent transformations as shown in Reaction Scheme 1 and Reaction Scheme 2.

Compounds of Formula 1 can be prepared by the methods outlined in Reaction Scheme 1 and Reaction Scheme 2. Reaction Scheme 2 is a general procedure that can be used to prepare all compounds embodied by Formula 1, but in the present case, it is particularly useful in the preparation of compounds where $R_1$ is varied while $R_2$ and $R_3$ are limited to cycloalkyl and $R_4$ is hydrogen. Reaction Scheme 1 is used in the preparation of compounds of Formula I-A.

In Reaction Scheme 2, an N-protected-amino acid 3 (see Reaction Scheme 3) is converted to a mixed anhydride on treatment with 2,6-dichlorobenzoyl chloride in the presence of Wang resin 2 and a proton acceptor, such as triethylamine, diisopropylethylamine or pyridine, preferably pyridine to give the resin bound amino acid of structure 4. The reaction is conveniently carried out in an inert solvent for example N,N-dimethylformamide or N-methylpyrrolidinone, preferably N-methylpyrrolidinone at from zero degrees to room temperature, most conveniently at room temperature. The conversion of 4 to the resin bound compound of structure 6 can be achieved by using the protocol outlined in method B. Thus after N-deprotection of the resin bound amino acid of structure 4 with piperidine in N,N-dimethylformamide, the product is then acylated with the $N^\alpha$-protected amino acid of structure 5 in the presence of diisopropylcarbodiimide and HOBT in N-methylpyrrolidinone. The deprotection and N-acylation is carried out at a temperature between about zero degrees and about room temperature, preferably at about room temperature. By using the coupling cycle described above for the conversion of 4 to 6 the N$^\alpha$-protected amino acids of structure 7 is incorporated into the resin bound compound of structure 6. Thus compounds of structure 6 are sequentially deprotected with piperidine in N,N-dimethylformamide and then coupled with compounds of structure 7 in the presence of diisopropylcarbodiimide and 1-hydroxybenzotriazole in N-methylpyrrolidinone at a temperature between about zero degrees and about room temperature, preferably at about room temperature to afford the resin bound compounds of structure 8.

The N-terminus protecting group PG$_2$ in the compounds of structure 8 was removed on treatment with a secondary amine base, preferably piperidine in an inert solvent (preferably N,N-dimethylformamide) and then was reacted with phosgene or a phosgene equivalent reagent, to ultimately yield in a two step sequence, the 2,5-dioxoimidazolidines of structure 10. The reaction to give the intermediate isocyanate 9 is conveniently carried out using trichloromethyl chloroformate (diphosgene) in an inert solvent, for example, a halogenated hydrocarbon in the presence of a proton acceptor, for example, pyridine, triethylamine or diisopropylethylamine, preferably diisopropylethylamine at a temperature between about zero degrees and about room temperature, preferably at about room temperature. The thermally induced cyclization of the intermediate isocyanates is performed by heating a suspension of the resin bound isocyanates of structure 9 in an inert solvent, for example toluene, at a temperature of from between 50° C. and the reflux temperature of the mixture, preferably at about 70° C. to give the resin bound compounds of structure 10.

Cleavage of the assembled peptidic residue 10 from the solid support to give the acids of structure 11 is achieved by shaking a suspension of 10 in a strong acid, for example methanesulfonic acid, hydrofluoric acid or trifluoroacetic acid, preferably trifluoroacetic acid optionally in the presence of a cation scavenger and an inert co-solvent, for example dichloromethane. The reaction is conveniently run at a temperature between about zero degrees and about room temperature, preferably at about room temperature.

To complete the synthesis, the acid of structure 11 is reacted with an alcohol (R$_6$OH) to form the ester 1. The esterification can be accomplished using many of the methods well known to those of average skill in the field of organic chemistry. The conversion is conveniently carried out using a coupling reagent, for example one of the many useful carbodiimides, preferably the water soluble 1-(3-dimethylaminopropyl)-3-ethylcarbodiimide, optionally using R$_6$OH or a mixture of R$_6$OH and a inert co-solvent, e.g., dichloromethane, as the reaction medium. The reaction is run at a temperature between about zero degrees and about room temperature, preferably at about room temperature.

In a similar fashion, Reaction Scheme 1, the N$^\alpha$-protected amino acids of structure 5 is converted to a mixed anhydride on treatment with 2,6-dichlorobenzoyl chloride in the presence of Wang resin 2 and a proton acceptor, such as triethylamine, diisopropylethylamine or pyridine, preferably pyridine to give the resin bound amino acid of structure 12. The reaction is conveniently carried out in an inert solvent for example N,N-dimethylformamide or N-methylpyrrolidinone, preferably N-methylpyrrolidinone at from zero degrees to room temperature, most conveniently at room temperature. The conversion of 12 to the resin bound compound of structure 13 can be achieved by using the protocol outlined in method B. Thus after N-deprotection of the resin bound amino acid of structure 12 with piperidine in N,N-dimethylformamide, the product is then acylated with the N$^\alpha$-protected amino acid of structure 7 in the presence of diisopropylcarbodiimide and HOBT in N-methylpyrrolidinone. The deprotection and N-acylation is carried out at a temperature between about zero degrees and about room temperature, preferably at about room temperature.

The N-terminus protecting group PG$_2$ in the compounds of structure 13 was removed on treatment with a secondary amine base, preferably piperidine in an inert solvent, preferably N,N-dimethylformamide and then was reacted with phosgene or a phosgene equivalent reagent, to ultimately yield in a two step sequence, the 2,5-dioxoimidazolidines of structure 15. The reaction to give the intermediate isocyanate 14 is conveniently carried out using trichloromethyl chloroformate (diphosgene) in an inert solvent, for example, a halogenated hydrocarbon in the presence of a proton acceptor, for example, pyridine, triethylamine or diisopropylethylamine, preferably diisopropylethylamine at a temperature between about zero degrees and about room temperature, preferably at about room temperature. The thermally induced cyclization of the intermediate isocyanates is accomplished by heating a suspension of the resin bound isocyanates of structure 14 in an inert solvent, for example toluene, at a temperature of from between 50° C. and the reflux temperature of the mixture, preferably at about 70° C. to give the resin bound compounds of structure 15.

Cleavage of the peptidic residue 15 from the solid support to give the acids of structure 16 is achieved by shaking a suspension of 15 in a strong acid, for example methanesulfonic acid, hydrofluoric acid or trifluoroacetic acid, preferably trifluoroacetic acid optionally in the presence of a cation scavenger and an inert co-solvent, for example dichloromethane. The reaction is conveniently run at a temperature of between about zero degrees and about room temperature, preferably at about room temperature.

Reaction of the acid 16 with R$_1$—NH$_2$ to form the amide of Formula 1 can be carried out under the coupling conditions previously described. The preferred coupling reagent in this instance is HBTU. The reaction is carried out in the presence of a tertiary amine base, such as triethylamine or diisopropylethylamine, preferably diisopropylethylamine in an inert solvent, for example N,N-dimethylformamide or N-methylpyrrolidinone, preferably N-methylpyrrolidinone at from zero degrees to room temperature, most conveniently at room temperature.

Reaction Scheme 3 outlines the preparation of the intermediate N-Fmoc-2-aminothiazole-4-carboxylic acid 3. Initially 9-fluorenylmethoxycarbonyl chloride (18) is reacted with potassium thiocyanate in an inert solvent, preferably ethyl acetate at a temperature of between zero degrees and 5° C. Then the reaction is allowed to proceed at a temperature of from zero degrees to 40° C., preferably at room temperature to furnish N-Fmoc-thiocyanate (19). Treatment of 19 with a solution of ammonia in an inert solvent, for example methanol or ethanol, preferably methanol at a temperature of from zero degrees to room temperature, preferably zero degrees afforded N-Fmoc-thiourea 20. In the final step, the thiourea 20 is then reacted with bromopyruvic acid to form the thiazole of structure 3. The reaction is conveniently carried out if an inert solvent, such as a cyclic ether, for example tetrahydrofuran or dioxane, preferably dioxane at a temperature of from 40° C. to the reflux temperature of the mixture preferably at about 70° C.

All of the compounds of Formula I which include the compounds set forth in the Examples, activated glucokinase in vitro by the procedure of Example A. In this manner, they increase the flux of glucose metabolism which causes increased insulin secretion. Therefore, the compounds of Formula I are glucokinase activators useful for increasing insulin secretion.

SYNTHESIS EXAMPLES

These examples are provided in illustration and are not intended to limit the invention in any way.

Analytical high performance liquid chromatography was (HPLC) was conducted on a Hewlett-Packard 1090 system with ultraviolet (UV) detection system at 214 nm using an ES Industries $C_{18}$ column (30×3.2 mm). Preparative HPLC separations were carried out using a Shimazu VP series system interfaced with a Perkin-Elmer Sciex Mass Spectrometer detector (PE Sciex 150EX) using a YMC $C_{18}$ column (2×5 cm).

Example 1
Preparation of N-Fmoc-thiourea

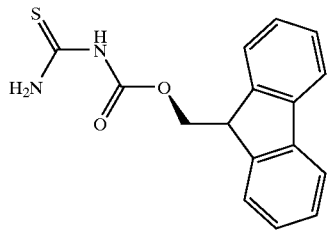

To a suspension of potassium thiocyanate (8.55 g, 88 mmol) in ethyl acetate (100 mL) cooled to 0° C. was added dropwise a solution of 9-fluorenylmethoxycarbonyl chloride (20.7 g, 80 mmol) in ethyl acetate (100 mL) over a period of 15 min. The resulting suspension was allowed to warm to ambient temperature overnight with stirring. The formed solid was filtered off and the filtrate was concentrated in vacuo to afford an orange oil. Without further purification, the oil was dissolved in ethanol (50 mL) and treated by dropwise addition with a cold solution of ammonia in ethanol (7N, 91 mL, 637 mmol). A precipitate formed upon addition of the ammonia solution. The suspension was stirred vigorously at 0° C. for 15 min and then the solids were filtered off, washed with cold ethanol (3×20 mL) and dried to afford N-Fmoc-thiourea (16.8 g, 70%) as an off-white solid: EI-HRMS m/e calcd for $C_{16}H_{14}N_2O_2S$ ($M^+$) 298.0776, found 298.0770.

Example 2
Preparation of N-Fmoc-2-aminothiazole-4-carboxylic acid

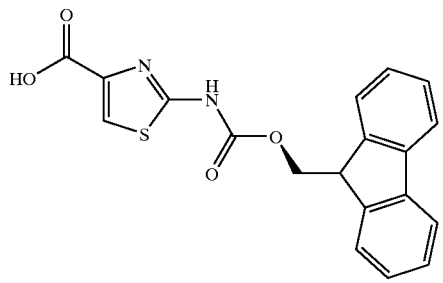

A solution of N-Fmoc-thiourea (5.96 g, 20 mmol) in dioxane (40 mL) was treated with bromopyruvic acid (3.34 g, 20 mmol). The reaction mixture was refluxed for 1 h, then the precipitated solids were recovered by filtration and washed with diethyl ether (3×20 mL) to afford N-Fmoc-2-aminothiazole-4-carboxylic acid (7.1 g, 97%) as a white solid: EI-HRMS m/e calcd for $C_{19}H_{14}N_2O_4S$ ($M^+$) 366.0674, found 366.0679.

Example 3
Preparation of (S)-2-[[3-cyclohexyl-2-(4,4-dimethyl-2,5-dioxoimidazolidin-1-yl)propanoyl]amino]thiazole-4-carboxylic acid methyl ester.

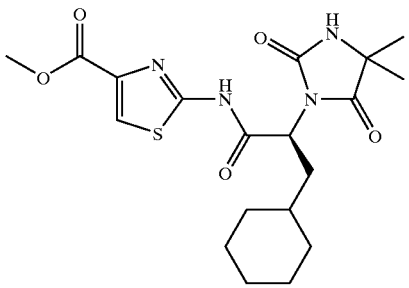

Step (i). A mixture of N-Fmoc-2-aminothiazole-4-carboxylic acid (6.0 g, 16.5 mmol), 2,6-dichlorobenzoyl chloride (7.9 mL, 55 mmol) in N-methylpyrrolidinone (50 mL) was added into a fritted polypropylene column charged with Wang resin (Midwest Bio-Tech, 10 g, 11 mmol). After the suspension was shaken for 5 min, pyridine (6.2 mL, 77 mmol) was added slowly and the resulting dark mixture was shaken overnight at ambient temperature. The mixture was then filtered and the resin was washed with N,N-dimethylformamide (3×100 mL), methanol (3×100 mL), dichloromethane (3×100 mL) and dried in vacuo.

Step (ii). To the resin product of the previous step (3 g, 2.31 mmol) was added 20% piperidine in N,N-dimethylformamide (25 mL). The reaction mixture was shaken at ambient temperature for 30 min. The mixture was filtered and the resin was washed with N,N-dimethylformamide (3×30 mL), methanol (3×30 mL), dichloromethane (3×30 mL). The resin was then suspended in N-methylpyrrolidinone (10 mL) and N-Fmoc-3-cyclohexyl-L-alanine (2.7 g, 6.93 mmol), diisopropylcarbodiimide (1.09 mL, 6.93 mmol) and HOBT (0.936 g, 6.93 mmol) were added. The resulting mixture was shaken at ambient temperature overnight and filtered. The resin was washed with N,N-dimethylformamide (3×100 mL), methanol (3×100 mL), dichloromethane (3×100 mL) and dried in vacuo.

Step (iii). To the resin product of the previous step (200 mg, 0.14 mmol) was added 20% piperidine in N,N-dimethylformamide (5 mL) and the reaction mixture was shaken at ambient temperature for 30 min. The mixture was filtered and the resin was washed with N,N-dimethylformamide (3×10 mL), methanol (3×10 mL), dichloromethane (3×10 mL). The resin was then suspended in N-methylpyrrolidinone (2 mL) N-Fmoc-2-amino-2-methylpropanoic acid (136 mg, 0.42 mmol), diisopropylcarbodiimide (65 μL, 0.42 mmol) and HOBT (57 mg, 0.42 mmol) were added. The resulting mixture was shaken at ambient temperature overnight and filtered. The resin was washed with N,N-dimethylformamide (3×10 mL), methanol (3×10 mL), dichloromethane (3×10 mL) and dried in vacuo.

Step (iv). To the product of the previous step (0.14 mmol) was added 20% piperidine in N,N-dimethylformamide (5 mL) and the reaction mixture was shaken at ambient temperature for 30 min. The mixture was filtered and the resin was washed with N,N-dimethylformamide (3×10 mL), methanol (3×10 mL), dichloromethane (3×10 mL). The resin was then suspended in dichloromethane (2 mL) and treated with diisopropylethylamine (73 μL, 0.42 mmol). The reaction mixture was then cooled to 0° C. and diphosgene (50 μL, 0.42 mmol) was added dropwise. The resulting mixture was allowed to warm to the ambient temperature and was stirred for 3 h. The mixture was filtered and the resin was washed with dichloromethane (3×10 mL) and dried in vacuo. The resin was then suspended in toluene (2 mL) and stirred reaction mixture was heated at 70° C. for 4 h. The cooled resin mixture was filtered and the resin was washed with dichloromethane (3×10 mL). Cleavage from the support was effected by treatment with 50% trifluoroacetic acid in dichloromethane (3 mL) for 1 hr. Concentration of the filtrate yielded a brown solid.

Step (v). Without further purification, the solid from Step (iv) was dissolved in methanol (1 mL) and then treated with 1-(3-dimethylaminopropyl)-3-ethylcarbodiimide (40 mg, 0.21 mmol). The mixture was stirred at ambient temperature overnight and then was concentrated in vacuo. The resulting oil was triturated with 99/1 dichloromethane/methanol (3×5 mL) and filtered through a silica gel plug. The filtrate was concentrated in vacuo to afford (S)-2-[[3-cyclohexyl-2-(4,4-dimethyl-2,5-dioxoimidazolidin-1-yl)propanoyl]amino]thiazole-4-carboxylic acid methyl ester (18 mg) as a white foam: EI-HRMS m/e calcd for $C_{19}H_{26}N_4O_5S$ ($M^+$) 423.1702, found 423.1701.

Example 4
Preparation of (S,S)-2-[[3-cyclohexyl-2-[4-(cyclohexyl)methyl-2,5-dioxoimidazolidin-1-yl]propanoyl]amino]thiazole-4-carboxylic acid methyl ester.

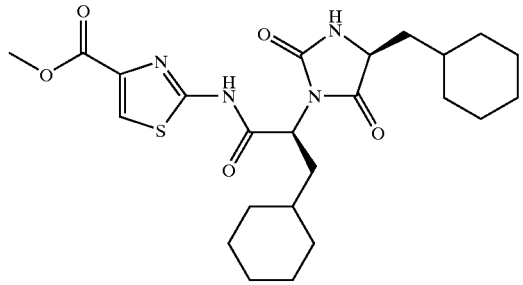

The compound was prepared as described in Example 3, except N-Fmoc-3-cyclohexyl-L-alanine was the amino acid incorporated in Step (iii) of the procedure. The title compound was obtained as a white foam: EI-HRMS m/e calcd for $C_{24}H_{34}N_4O_5S$ ($M^+$) 491.2328, found 491.2323.

Example 5
Preparation of (S,S)-2-[[3-cyclohexyl-2-[2,5-dioxo-4-(naphthalen-2-yl)methylimidazolidin-1-yl]propanoyl]amino]thiazole-4-carboxylic acid methyl ester.

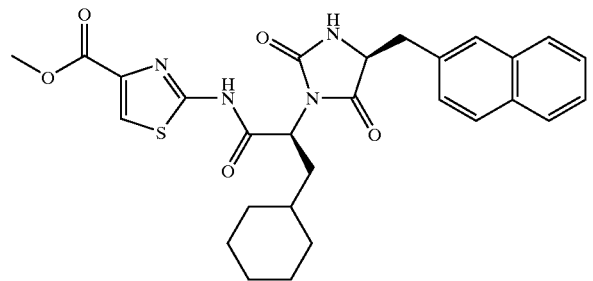

The compound was prepared as described in Example 3, except N-Fmoc-3-(naphthalen-2-yl)-L-alanine was the amino acid incorporated in Step (iii) of the procedure. The title compound was obtained as a white foam: EI-HRMS m/e calcd for $C_{28}H_{30}N_4O_5S$ ($M^+$) 535.2015, found 535.2035.

Example 6
Preparation of 2-[[(S)-2-[(R)-4-(4-chlorobenzyl)-2,5-dioxoimidazolidin-1-yl]-3-cyclohexylpropanoyl]amino]thiazole-4-carboxylic acid methyl ester.

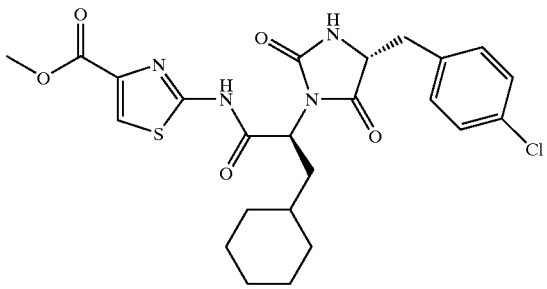

The compound was prepared as described in Example 3, except N-Fmoc-3-(4-chlorophenyl)-D-alanine was the amino acid incorporated in Step (iii) of the procedure. The title compound was obtained as a white foam: EI-HRMS m/e calcd for $C_{24}H_{27}N_4O_5SCl$ ($M^+$) 519.1469, found 519.1466.

Example 7
Preparation of (S,S)-2-[[3-cyclohexyl-2-[2,5-dioxo-4-(4-hydroxybenzyl)imidazolidin-1-yl]propanoyl]amino]thiazole-4-carboxylic acid methyl ester.

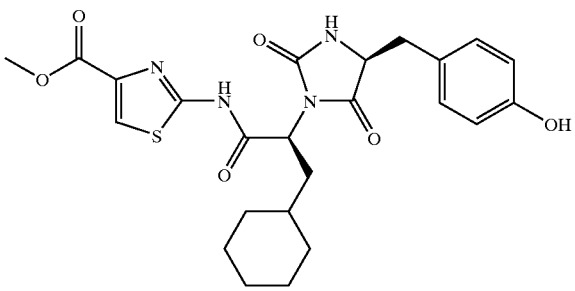

The compound was prepared as described in Example 3, except N-Fmoc-L-tyrosine was the amino acid incorporated in Step (iii) of the procedure. The title compound was obtained as a white foam: EI-HRMS m/e calcd for $C_{24}H_{28}N_4O_6S$ ($M^+$) 501.1808, found 501.1815.

Example 8
Preparation of (S)-2-[[3-cyclohexyl-2-(2,4-dioxo-1,3-diazaspiro[4.4]non-3-yl)propanoyl]amino]thiazole-4-carboxylic acid methyl ester.

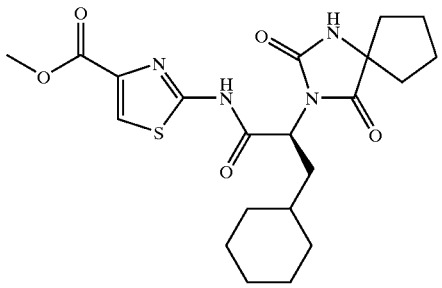

The compound was prepared as described in Example 3, except N-Fmoc-1-aminocyclopentanecarboxylic acid was the amino acid incorporated in Step (iii) of the procedure: EI-HRMS m/e calcd for $C_{21}H_{28}N_4O_5S$ (M$^+$) 449.1859, found 449.1853.

Example 9

Preparation of (S,S)-2-[[3-cyclohexyl-2-[2,5-dioxo-4-(3-hydroxybenzyl)imidazolidin-1-yl]propanoyl]amino]thiazole-4-carboxylic acid methyl ester.

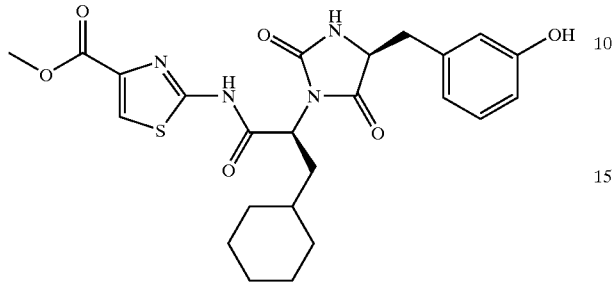

The compound was prepared as described in Example 3, except N-Fmoc-3-(3-hydroxyphenyl)-L-alanine was the amino acid incorporated in Step (iii) of the procedure: EI-HRMS m/e calcd for $C_{24}H_{28}N_4O_6S$ (M$^+$) 501.1808, found 501.1816.

Example 10

Preparation of 2-[[(S)-3-cyclohexyl-2-[(R,S)-2,5-dioxo-4-(4-fluorobenzyl)imidazolidin-1-yl]propanoyl]amino]thiazole-4-carboxylic acid methyl ester.

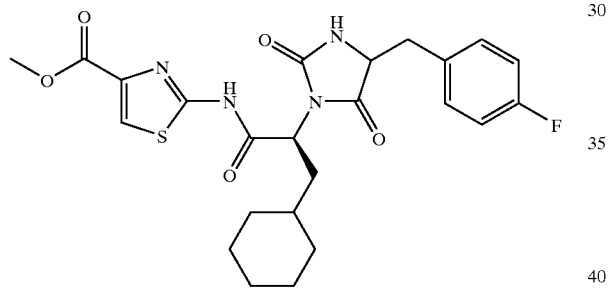

The compound was prepared as described in Example 3, except N-Fmoc-3-(4-fluorophenyl)-DL-alanine was the amino acid incorporated in Step (iii) of the procedure: EI-HRMS m/e calcd for $C_{24}H_{27}N_4O_5SF$ (M$^+$) 503.1764, found 503.1776.

Example 11

Preparation of (S,S)-2-[[3-cyclohexyl-2-[2,5-dioxo-4-(thiophen-2-yl)methylimidazolidin-1-yl]propanoyl]amino]thiazole-4-carboxylic acid methyl ester.

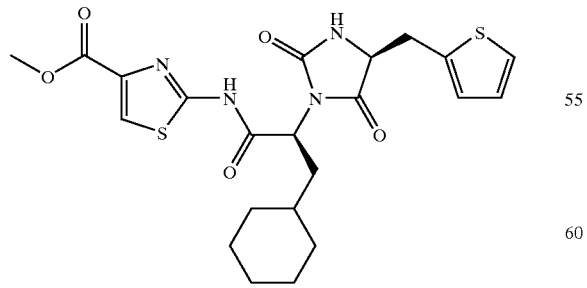

The compound was prepared as described in Example 3, except N-Fmoc-3-(thiophen-2-yl)-L-alanine was the amino acid incorporated in Step (iii) of the procedure: EI-HRMS m/e calcd for $C_{22}H_{26}N_4O_5S_2$ (M$^+$) 491.1423, found 491.1425.

Example 12

Preparation of 2-[[(S)-3-cyclohexyl-2-[(R)-2,5-dioxo-4-propylimidazolidin-1-yl]propanoyl]amino]thiazole-4-carboxylic acid methyl ester

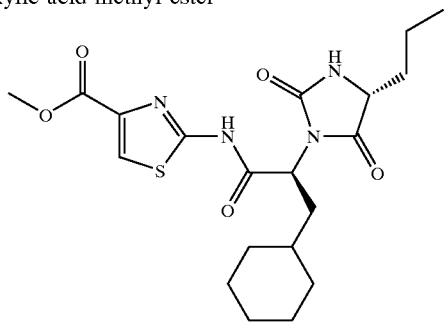

The compound was prepared as described in Example 3, except (R)-N-Fmoc-2-aminopentanoic acid was the amino acid incorporated in Step (iii) of the procedure: EI-HRMS m/e calcd for $C_{20}H_{28}N_4O_5S$ (M$^+$) 437.1859, found 437.1850.

Example 13

Preparation of (S,S)-2-[[2-(4-benzyl-2,5-dioxoimidazolidin-1-yl)-3-cyclohexylpropanoyl]amino]thiazole-4-carboxylic acid methyl ester.

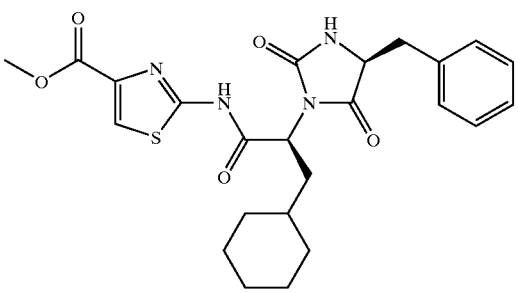

The compound was prepared as described in Example 3, except N-Fmoc-L-phenylalanine was the amino acid incorporated in Step (iii) of the procedure: EI-HRMS m/e calcd for $C_{24}H_{28}N_4O_5S$ (M$^+$) 485.1859, found 485.1857.

Example 14

Preparation of (S,S)-2-[[3-cyclohexyl-2-[4-(cyclopentyl)methyl-2,5-dioxoimidazolidin-1-yl]propanoyl]amino]thiazole-4-carboxylic acid methyl ester.

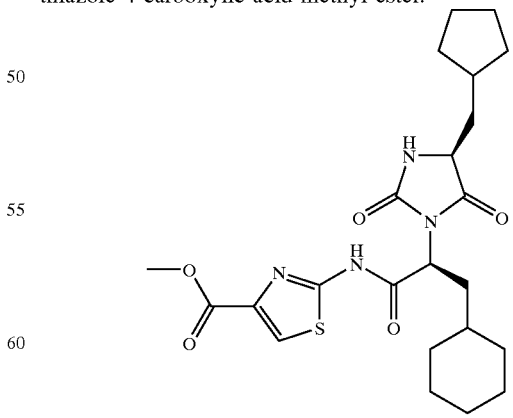

The compound was prepared as described in Example 3, except N-Fmoc-3-cyclopentyl-L-alanine was the amino acid incorporated in Step (iii) of the procedure: EI-HRMS m/e calcd for $C_{23}H_{32}N_4O_5S$ (M$^+$) 477.2172, found 477.2170.

Example 15

Preparation of (S,S)-2-[[3-cyclopentyl-2-[4-(cyclopentyl)methyl-2,5-dioxoimidazolidin-1-yl]propanoyl]amino]thiazole-4-carboxylic acid methyl ester.

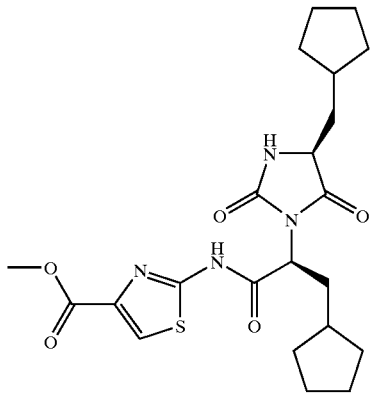

The compound was prepared as described in Example 3, except N-Fmoc-3-cyclopentyl-L-alanine was the amino acid incorporated in both Step (ii) and Step (iii) of the procedure. The title compound was obtained as a white foam: EI-HRMS m/e calcd for $C_{22}H_{30}N_4O_5S$ (M$^+$) 463.2015, found 463.2023.

Example 16

Preparation of (S,S)-2-[[2-[4-(cyclohexyl)methyl-2,5-dioxoimidazolidin-1-yl]-3-cyclopentylpropanoyl]amino]thiazole-4-carboxylic acid methyl ester.

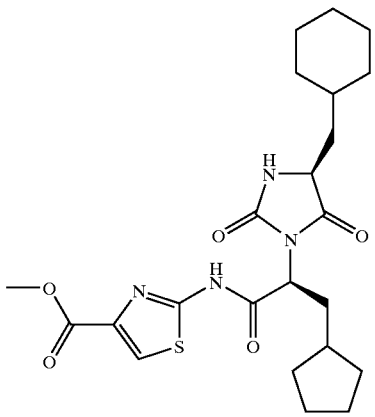

The compound was prepared as described in Example 3, except N-Fmoc-3-cyclopentyl-L-alanine and N-Fmoc-3-cyclohexyl-L-alanine were the amino acids incorporated in Step (ii) and Step (iii) of the procedure respectively: EI-HRMS m/e calcd for $C_{23}H_{32}N_4O_5S$ (M$^+$) 477.2172, found 477.2164.

Example 17

Preparation of (S,S)-3-cyclohexyl-2-[4-(cyclohexyl)methyl-2,5-dioxoimidazolidin-1-yl]-N-(thiazol-2-yl)propanamide:

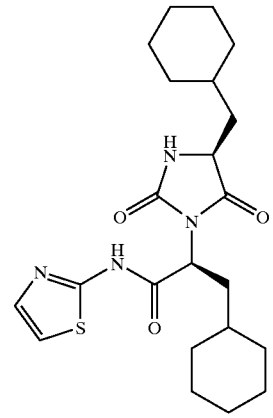

Step (i). A mixture of N-Fmoc-3-cyclohexyl-L-alanine (3.47 g, 8.8 mmol), 2,6-dichlorobenzoyl chloride (3.2 mL, 22 mmol) in N-methylpyrrolidinone (20 mL) was added into a fritted polypropylene column charged with Wang resin (Midwest Bio-Tech, 4 g, 4.4 mmol). The suspension was shaken for 5 min, then pyridine (2.5 mL, 30.8 mmol) was then added slowly and the resulting dark mixture was shaken overnight at ambient temperature. The mixture was then filtered and the resin was washed with N,N-dimethylformamide (3×30 mL), methanol (3×30 mL), dichloromethane (3×30 mL) and dried in vacuo.

Step (ii). To the resin product of step (i) was added 20% piperidine in N,N-dimethylformamide (25 mL) and the reaction mixture was shaken at ambient temperature for 30 min. The mixture was filtered and the resin was washed with N,N-dimethylformamide (3×30 mL), methanol (3×30 mL), dichloromethane (3×30 mL). The resin was then suspended in N-methylpyrrolidinone (10 mL) and N-Fmoc-3-cyclohexyl-L-alanine (5.2 g, 13.2 mmol), diisopropylcarbodiimide (2.1 mL, 13.2 mmol) and HOBT (1.8 g, 13.2 mmol) were added. The resulting mixture was shaken at ambient temperature overnight and filtered. The resin was washed with N,N-dimethylformamide (3×30 mL), methanol (3×30 mL), dichloromethane (3×30 mL) and dried in vacuo.

Step (iii). To the resin product of Step (ii) was added 20% piperidine in N,N-dimethylformamide (25 mL) and the reaction mixture was shaken at ambient temperature for 30 min. The mixture was filtered and the resin was washed with N,N-dimethylformamide (3×30 mL), methanol (3×30 mL), dichloromethane (3×30 mL). The resin was then suspended in dichloromethane (20 mL) and treated with diisopropylethylamine (2.3 mL, 13.2 mmol). The reaction mixture was then cooled to 0° C. and diphosgene (1.6 mL, 13.2 mmol) was added dropwise. The mixture was allowed to warm to room temperature with stirring for 5 h, then was filtered and the resin was washed with dichloromethane (3×30 mL) and dried in vacuo. The resin was then suspended in toluene (20 mL) and the stirred mixture was heated at 70° C. for 4 h. The cooled resin mixture was filtered and the resin was washed with dichloromethane (3×30 mL). Cleavage from the support was effected by treatment with 50% trifluoroacetic acid in dichloromethane (30 mL) for 1 hr. Concentration of the filtrate yielded a brown solid. It was then purified by reversed phase HPLC to afford (S,S)-3-cyclohexyl-2-[4-(cyclohexyl)methyl-2,5-dioxoimidazolidin-1-yl]propanoic acid (850 mg) as a white foam: EI-HRMS m/e calcd for $C_{19}H_{30}N_2O_4$ (M$^+$) 350.2205, found 350.2204.

Step (iv). A solution of (S,S)-3-cyclohexyl-2-[4-(cyclohexyl)methyl-2,5-dioxoimidazolidin-1-yl]propanoic acid [Step (iii); 25 mg, 0.071 mmol] in N-methylpyrrolidinone (1 mL) was treated with diisopropylethylamine (19 μL, 1.065 mmol) and HBTU (29.3 mg, 0.078 mmol). The reaction mixture was then treated with 2-aminothiazole (7.2 mg, 0.071 mmol) and stirred at ambient temperature overnight. The reaction mixture was then diluted with water (2 mL) and extracted with ethyl acetate (2×3 mL). The combined organic layers were dried over magnesium sulfate, filtered, and concentrated in vacuo. The product was purified by using flash chromatography (Merck Silica gel 60, 230–400 mesh, 99/1 dichloromethane/methanol) to furnish (S,S)-3-cyclohexyl-2-[4-(cyclohexyl)methyl-2,5-dioxoimidazolidin-1-yl]-N-(thiazol-2-yl)propanamide (27 mg, 88%) as a white foam: EI-HRMS m/e calcd. for $C_{22}H_{32}N_4O_3S$ (M$^+$) 433.2273, found 433.2270.

Example 18
Preparation of (S,S)-[2-[[3-cyclohexyl-2-[4-(cyclohexyl)methyl-2,5-dioxoimidazolidin-1-yl]propanoyl]amino]thiazol-4-yl]oxoacetic acid ethyl ester.

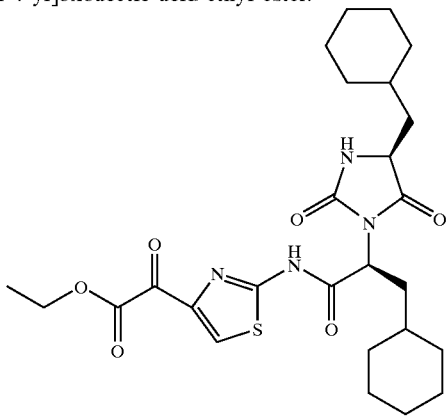

By using the conditions described in Step (iv) of Example 17, ethyl 2-amino-4-thiazoleglyoxylate was condensed with (S,S)-3-cyclohexyl-2-[4-(cyclohexyl)methyl-2,5-dioxoimidazolidinyl]propanoic acid [Example 17, Step (iii)] to give the title compound as a colorless foam: EI-HRMS m/e calcd. for $C_{26}H_{36}N_4O_6S$ (M$^+$) 533.2434, found 533.2431.

Example 19
Preparation of (S,S)-[2-[[3-cyclohexyl-2-[4-(cyclohexyl)methyl-2,5-dioxoimidazolidin-1-yl]propanoyl]amino]thiazol-4-yl]acetic acid ethyl ester.

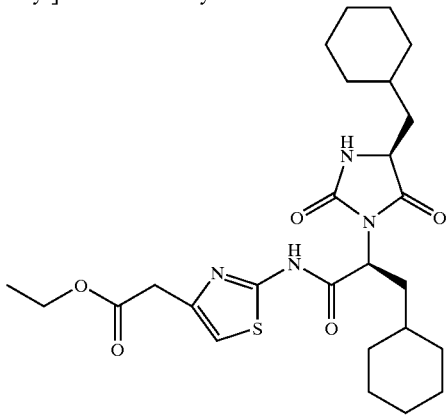

By using the conditions described in Step (iv) of Example 17, ethyl 2-amino-4-thiazoleacetate was condensed with (S,S)-3-cyclohexyl-2-[4-(cyclohexyl)methyl-2,5-dioxoimidazolidinyl]propanoic acid [Example 17, Step (iii)] to give the title compound as a colorless foam: EI-HRMS m/e calcd. for $C_{26}H_{38}N_4O_5S$ (M$^+$) 519.2641, found 519.2620.

Example 20
Preparation of (S,S)-3-cyclohexyl-2-[4-(cyclohexyl)methyl-2,5-dioxoimidazolidin-1-yl]-N-(5-methylpyridin-2-yl)propanamide.

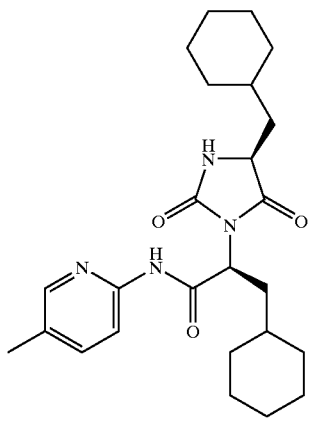

By using the conditions described in Step (iv) of Example 17, 2-amino-5-methylpyridine was condensed with (S,S)-3-cyclohexyl-2-[4-(cyclohexyl)methyl-2,5-dioxoimidazolidinyl]propanoic acid [Example 17, Step (iii)] to give the title compound as a colorless foam: EI-HRMS m/e calcd. for $C_{25}H_{36}N_4O_3$ (M$^+$) 441.2866, found 441.2869.

Example 21
Preparation of (S,S)-6-[[3-cyclohexyl-2-[4-(cyclohexyl)methyl-2,5-dioxoimidazolidin-1-yl]propanoyl]amino]nicotinic acid methyl ester.

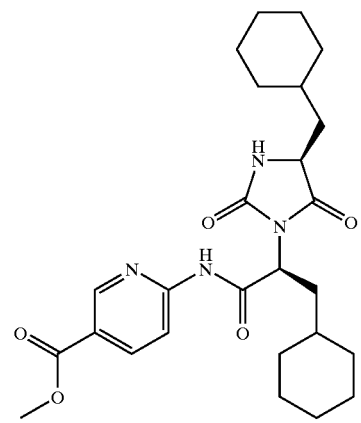

By using the conditions described in Step (iv) of Example 17, methyl 6-aminonicotinate was condensed with (S,S)-3-cyclohexyl-2-[4-(cyclohexyl)methyl-2,5-dioxoimidazolidinyl]propanoic acid [Example 17, Step (iii)] to give the title compound as a colorless foam: EI-HRMS m/e calcd for $C_{26}H_{36}N_4O_5$ (M$^+$) 485.2764, found 485.2768.

Example 22

Preparation of (S,S)-N-(5-chloropyridin-2-yl)-3-cyclohexyl-2-[4-(cyclohexyl)methyl-2,5-dioxoimidazolidin-1-yl]propanamide.

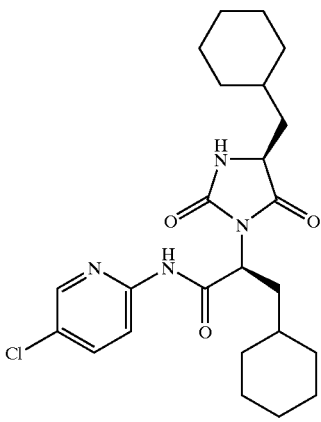

By using the conditions described in Step (iv) of Example 17, 2-amino-5-chloropyridine was condensed with (S,S)-3-cyclohexyl-2-[4-(cyclohexyl)methyl-2,5-dioxoimidazolidinyl]propanoic acid [Example 17, Step (iii)] to give the title compound as a colorless foam: EI-HRMS m/e calcd for $C_{24}H_{33}N_4O_3Cl$ (M$^+$) 461.2319, found 461.2321.

Example 23

Preparation of (S,S)-3-cyclohexyl-2-[4-(cyclohexyl)methyl-2,5-dioxoimidazolidin-1-yl]-N-(pyridin-2-yl)propanamide.

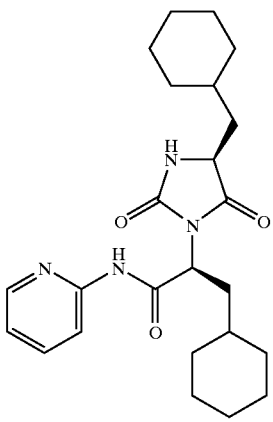

By using the conditions described in Step (iv) of Example 17, 2-aminopyridine was condensed with (S,S)-3-cyclohexyl-2-[4-(cyclohexyl)methyl-2,5-dioxoimidazolidinyl]propanoic acid [Example 17, Step (iii)] to give the title compound as a colorless foam: EI-HRMS m/e calcd for $C_{24}H_{34}N_4O_3$ (M$^+$) 427.2709, found 427.2706.

Biological Activity

Example A

Glucokinase Activity

Glucokinase Assay: Glucokinase (GK) was assayed by coupling the production of glucose-6-phosphate to the generation of NADH with glucose-6-phosphate dehydrogenase (G6PDH, 0.75-1 k units/mg; Boehringer Mannheim, Indianapolis, Ind.) from *Leuconostoc mesenteroides* as the coupling enzyme (Scheme 2).

Scheme 2

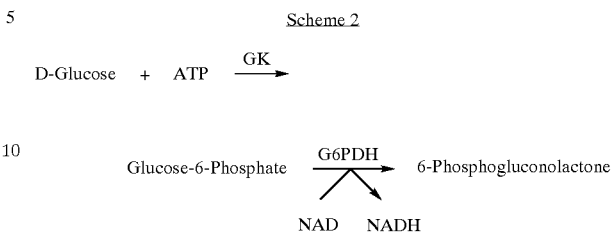

Recombinant human liver GK1 was expressed in *E. coli* as a glutathione S-transferase fusion protein (GST-GK) [Liang, Y., Kesavan, P., Wang, L., Niswender, K., Tanizawa, Y., Permut, M. A., Magnuson, M., and Matschinsky, F. M. Variable effects of maturity-onset-diabetes-of-youth (MODY)-associated glucokinase mutations on the substrate interactions and stability of the enzyme. *Biochem. J.* 309: 167–173, 1995] and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet, K., Keenan, R. P., and Tippett, P. S. Observation of a kinetic slow transition in monomeric glucokinase. *Biochemistry* 29; 770–777, 1990).

The assay was conducted at 25° C. in a flat bottom 96-well tissue culture plate from Costar (Cambridge, Mass.) with a final incubation volume of 120 µl. The incubation mixture contained: 25 mM Hepes buffer (pH, 7.1), 25 mM KCl, 5 mM D-glucose, 1 mM ATP, 1.8 mM NAD, 2 mM MgCl$_2$, 1 µM sorbitol-6-phosphate, 1 mM dithiothreitol, test drug or 10% DMSO, 1.8 unit/mL G6PDH, and GK (see below). All organic reagents were >98% pure and were from Boehringer Mannheim with the exceptions of D-glucose and Hepes that were from Sigma Chemical Co, St. Louis, Mo. Test compounds were dissolved in DMSO and were added to the incubation mixture minus GST-GK in a volume of 12 µl to yield a final DMSO concentration of 10%. This mix was preincubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 µl GST-GK.

After addition of enzyme, the increase in optical density (OD) at 340 nm was monitored over a 10 minute incubation period as a measure of GK activity. Sufficient GST-GK was added to produce an increase in OD$_{340}$ of 0.08 to 0.1 units over the 10 minute incubation period in wells containing 10% DMSO, but no test compound. Preliminary experiments established that the GK reaction was linear over this period of time even in the presence of activators that produced a 5-fold increase in GK activity. The GK activity in control wells was compared with the activity in wells containing test GK activators, and the concentration of activator that produced a 50% increase in the activity of GK, i.e., the SC$_{1.5}$, was calculated.

All of the compounds of Formula I described in the Synthesis Examples had an SC$_{1.5}$ less than or equal to 30 µM.

What is claimed is:

1. A compound of the formula:

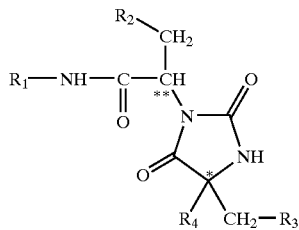

wherein

R₁ is a five- or six-membered aromatic heterocyclic ring having one to three heteroatoms selected from nitrogen, oxygen, and sulfur, which ring is unsubstituted or substituted with halo, amino, hydroxylamino, nitro, cyano, sulfonamido, lower alkyl, perfluoro lower alkyl, lower alkyl thio, perfluoro-lower alkyl thio, lower alkyl sulfonyl, perfluoro-lower alkyl sulfonyl, lower alkyl sulfinyl, or —(R₅)ₙ—C(O)—OR₆;

R₂ is a cycloalkyl ring containing from 5 to 7 carbon atoms;

R₃ is an unsubstituted five- or six-membered aromatic heterocyclic ring having one or two heteroatoms selected from nitrogen, oxygen, and sulfur;

R₄ is hydrogen or lower alkyl;

R₅ is —C(O)— or lower alkyl;

R₆ is lower alkyl;

n is 0 or 1; * and ** each designate an asymmetric centers or a pharmaceutically acceptable salt thereof.

2. The compound of claim 1 wherein R₁ is substituted or unsubstituted thiazolyl.

3. The compound of claim 2 wherein R₁ is substituted thiazolyl.

4. The compound of claim 3 wherein R₁ is thiazolyl substituted with —(R₅)ₙ—C(O)—OR₆.

5. The compound of claim 4 wherein R₂ is cyclopentyl or cyclohexyl.

6. A compound of claim 5 which is (S,S)-2-[[3-cyclohexyl-2-[2,5-dioxo-4-(thiophen-2yl) methylimidazolidin-1-yl]propanoyl]amino]thiazole-4-carboxylic acid methyl ester.

7. A compound of claim 1 wherein R₁ is substituted or unsubstituted pyridine.

8. A compound of claim 7 wherein R₂ is cyclohexyl.

* * * * *